United States Patent
Dobelin

(10) Patent No.: US 6,652,813 B1
(45) Date of Patent: Nov. 25, 2003

(54) REACTION CHAMBER SYSTEM FOR CHEMICAL SYNTHESIS OR RELATED APPLICATIONS

(75) Inventor: Werner Dobelin, Reinach (CH)

(73) Assignee: Hettlab AG, Bach (CH)

( * ) Notice: Subject to any disclaimer, the term of this patent is extended or adjusted under 35 U.S.C. 154(b) by 0 days.

(21) Appl. No.: 09/308,067
(22) PCT Filed: Nov. 13, 1997
(86) PCT No.: PCT/CH97/00431
§ 371 (c)(1), (2), (4) Date: Jul. 12, 1999
(87) PCT Pub. No.: WO98/20965
PCT Pub. Date: May 22, 1998

(30) Foreign Application Priority Data

Nov. 13, 1996 (CH) .............................................. 2811/96

(51) Int. Cl.⁷ ................................................. B01L 9/00
(52) U.S. Cl. ........................ 422/104; 422/99; 366/197; 366/208; 366/209; 366/273
(58) Field of Search ........................ 422/99, 100, 103, 422/104, 129, 130, 131, 132, 138; 436/174, 180, 809; 435/287, 305, 313, 315, 316; 366/273, 274, 197, 204, 208, 209, 211, 219, 237, 239

(56) References Cited

U.S. PATENT DOCUMENTS

| | | | |
|---|---|---|---|
| 3,622,128 A | 11/1971 | Geiser .......................... 259/56 |
| 4,925,629 A | 5/1990 | Schramm ..................... 422/82 |
| 5,229,075 A * | 7/1993 | Fauske ........................ 422/130 |
| 5,259,672 A * | 11/1993 | Rowe ........................ 366/111 |
| 5,302,347 A | 4/1994 | Van Den Berg et al. ...... 422/67 |
| 5,409,312 A * | 4/1995 | Fletcher ....................... 366/208 |
| 5,511,879 A * | 4/1996 | Fletcher ....................... 366/208 |
| 5,558,839 A * | 9/1996 | Matte et al. ................. 422/101 |
| 5,651,943 A * | 7/1997 | Lam et al. ................... 422/131 |
| 5,716,584 A * | 2/1998 | Baker et al. ................. 422/131 |
| 5,834,739 A * | 11/1998 | Lockwood et al. ......... 219/458 |
| 5,934,804 A * | 8/1999 | Branson et al. ............. 366/208 |
| 5,985,535 A * | 11/1999 | Urabe ......................... 430/569 |
| 6,076,957 A * | 6/2000 | Gomes ........................ 366/274 |
| 6,126,904 A * | 10/2000 | Zuellig et al. ............... 422/130 |
| 6,210,033 B1 * | 4/2001 | Karkos, Jr. et al. ......... 366/274 |

FOREIGN PATENT DOCUMENTS

WO 9633010 10/1996

* cited by examiner

Primary Examiner—Jill Warden
Assistant Examiner—Dwayne K. Handy
(74) Attorney, Agent, or Firm—Ladas & Parry

(57) ABSTRACT

In a reaction chamber is located a platform for receiving individual samples and sample racks. The reaction chamber can be heated, cooled and evacuated. The samples are then radiation heated. The sample platform is shaken by magnetic coupling. The individual sample containers/reaction containers may be filled or emptied in use thorough ducts. The system has applications in the field of chemical combinatory synthesis, as evaporator or for related applications.

8 Claims, 3 Drawing Sheets

REACTION CHAMBER SYSTEM FOR CHEMICAL SYNTHESIS OR RELATED APPLICATIONS

The invention deals with a reaction chamber system that can be used for simultaneously processing a multitude of liquid, or liquid solutions of aggressive or hazardous samples.

Processing a multitude of samples simultaneously presents difficulties that have hitherto not been resolved satisfactorily.

Aggressive or hazardous samples are usually processed individually. Known systems such as vacuum centrifuges are disadvantageous, since they require special sample racks and are suited only for certain processing steps (e.g. drying).

U.S. Pat. No. 4,925,629 discloses a sample processing device containing sample containers in the form of microplates arranged in an open container that can be shaken by an independent drive arranged underneath the container. Due to the open arrangement of the samples, this device is not suitable for processing aggressive or hazardous samples.

U.S. Pat. No. 3,622,128 shows a sample conveying device with an integrated mixing function that is active during transportation. This device is not a reaction chamber system that would be suitable for processing the mentioned problematic samples.

The object of the invention is therefore to disclose a reaction chamber system that is capable of simultaneously processing a multitude of samples and of handling several processing steps automatically as required, for example, in combinatorial chemical synthesis.

According to the invention, this object is solved by a reaction chamber system of the type declared in the beginning, characterized by a closed reaction chamber with a platform movably arranged inside the chamber for receiving individual sample containers, and by a shaking drive, located outside the reaction chamber, for driving the platform by magnetic coupling. The reaction chamber is suitably resistant to the samples as well as to temperature and can be evacuated. Radiant heaters, preferably placed outside the reaction chamber, heat the samples. Additionally and preferably, means are provided for filling and emptying the sample containers during processing.

Figure 1:
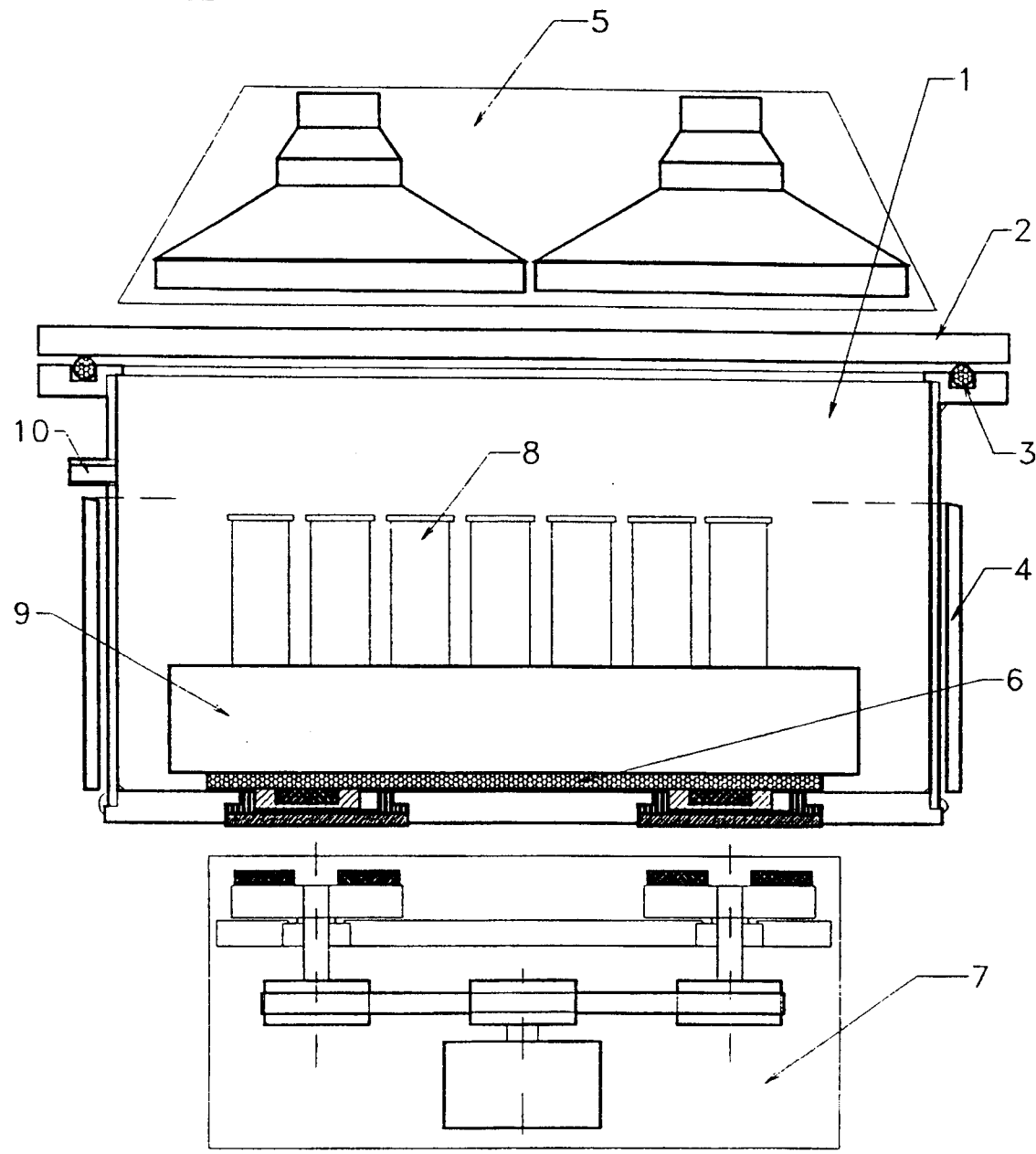

A preferred exemplary embodiment of the invention is described below with the help of attached drawings:

FIG. 1: a schematic representation of a reaction chamber system

Figure 2:
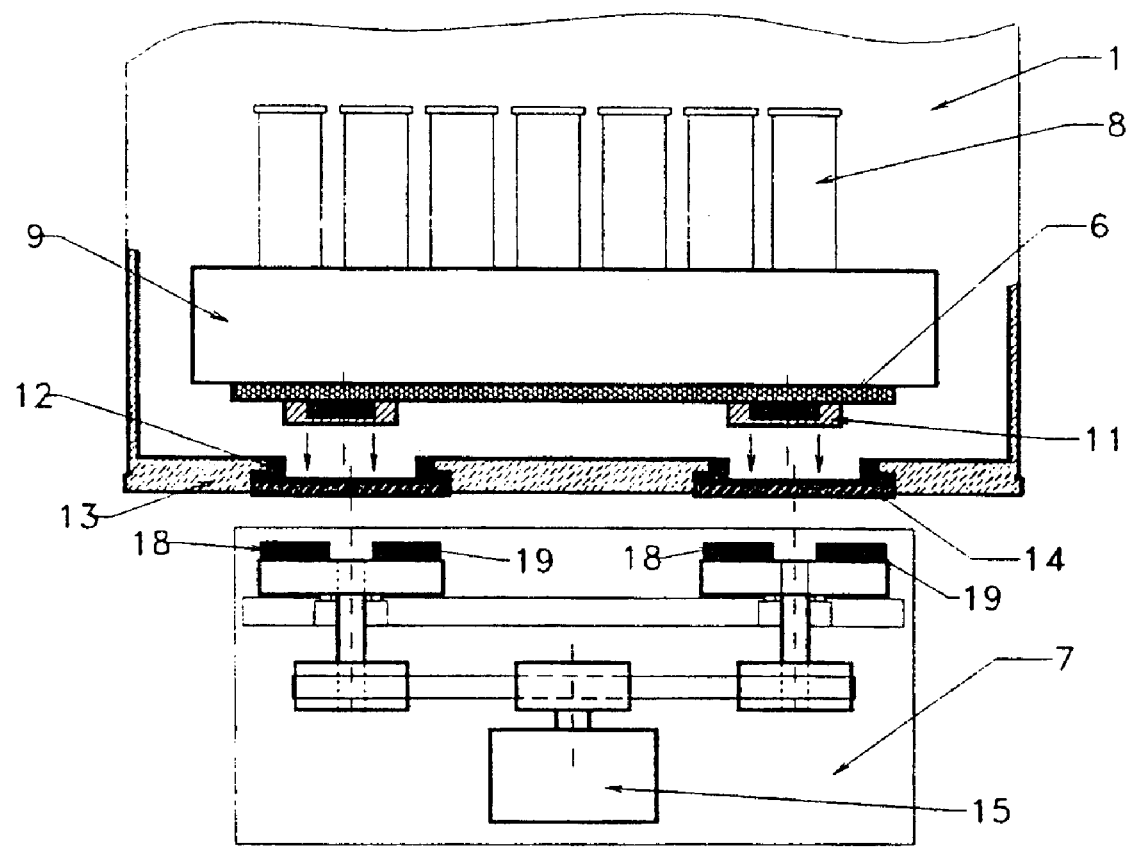

FIG. 2: shaking drive system as used in the system shown in FIG. 1

Figure 3:
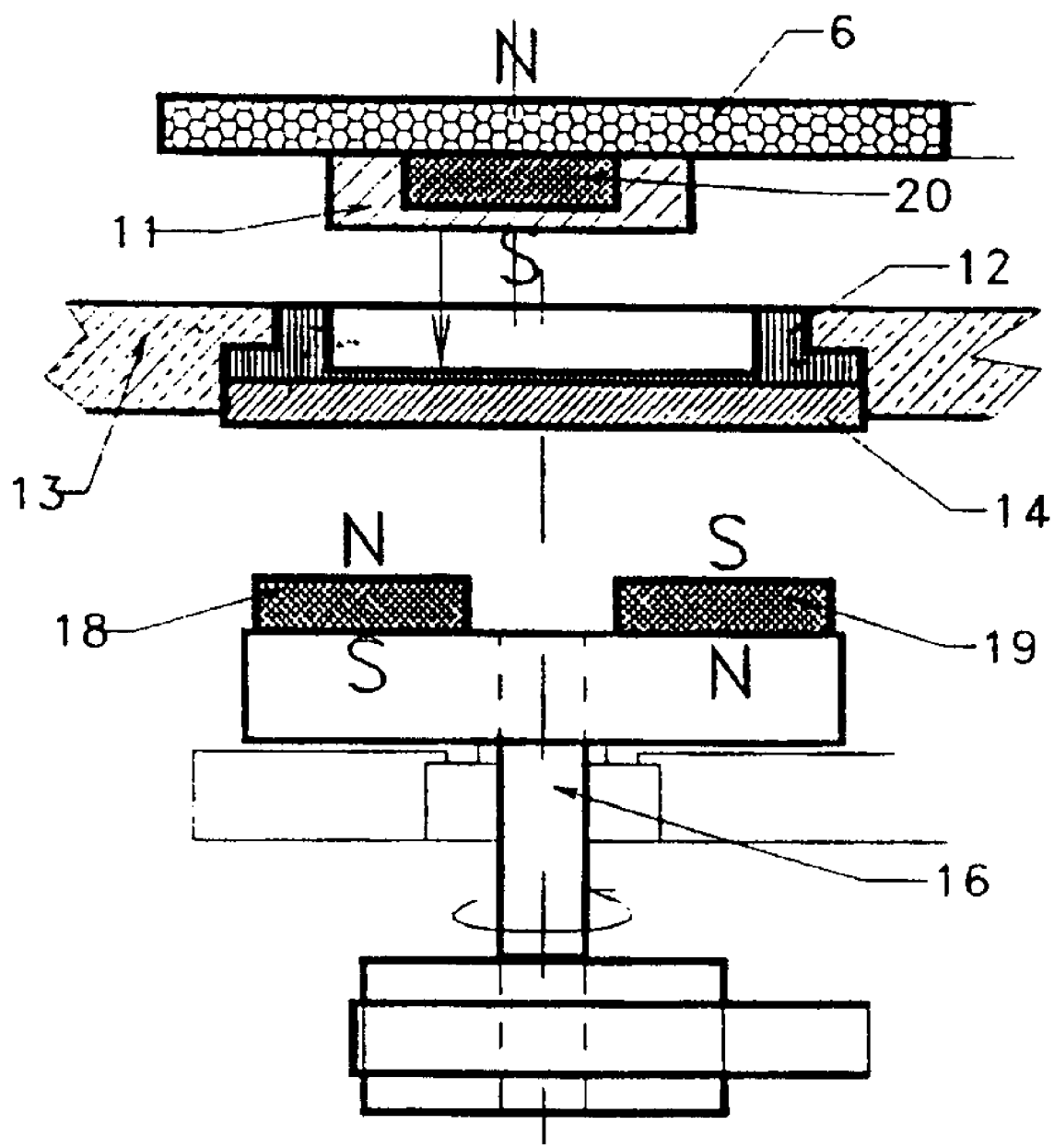

FIG. 3: a single magnetic coupling unit as used in the system shown in FIG. 2.

As shown in FIG. 1, a reaction chamber 1 is closed at the top by a glass plate 2, sealed by a seal 3 and heated by jacket heating 4. Additionally, an infrared radiator 5 can be used to heat the interior of the reaction chamber 1. Shaking drive 7 drives a shaking plate 6 located inside the reaction chamber 1. The construction of the shaking drive is shown in detail in FIGS. 2 and 3. Sample rack 9 complete with sample containers 8 is mounted on a shaking plate 6. Alternatively, sample rack 9 and shaking plate 6 may be integrated to form a single unit. Electrical, discharge, gas, vacuum, solvent, reagent and sensor lines are connected with the reaction chamber 1 by means of connections 10. FIG. 1 shows connections 10 and jacket heating 4 only schematically. It is understood that they are designed according to the state-of-the-art. Seal 3, glass plate 2 and infrared radiator 5 are not described in any detail either, since they are designed according to the appropriate state-of-the-art also.

As shown in FIG. 2, shaking plate 6 is fixed to bearing journal 11. Bearing shells 12 are mounted in the bottom plate 13 of the reaction chamber. Glass inserts 14 underneath the bearing shells 12 seal the reaction chamber 1. Outside the reaction chamber, motor 15 drives shaking drive 7 with drivers 16.

Bearing journals 11 mounted at shaking locations 6 are seated in bearing shells 12. For each shaking plate 6 at least three bearing journals 11 with the corresponding bearing shells 12 are required. The excursion of the shaking movement is determined by the difference between the ID of the bearing shell 12 and the OD of the bearing journal. Shaking plate 6 executes a circular motion. In order to obtain a high shaking frequency, electrically non-conducting glass inserts 14 are used in the otherwise metallic reaction chamber bottom plate 13. This prevents the braking effect due to eddy currents. Driver magnets 18/19 do not contact glass inserts 14.

As shown in FIG. 3, a shaking magnet 20 is embedded in bearing journal 11 and is therefore indirectly fixed to shaking plate 6. Bearing shell 12 and glass insert 14 sandwiched between driver magnets 18/19 and shaking magnet 20, are embedded in the reaction chamber bottom plate 13.

Shaking magnet 20 is attracted by driver magnet 18 and repelled by driver magnet 19, or vice versa depending on polarization.

Friction between the bearing surface in bearing shell 12 and the bearing face of the bearing journal 11 depends on the total shaking mass and the applied magnetic force.

As the RPM (rotations per minute) of the driver magnets 18/19 increase, the shaking magnet 20 increasingly lags behind and is further removed from the optimal position above the attracting driver magnet 18. Consequently, the shaking magnet 20 increasingly approaches the repelling magnet 19, which tends to lower friction and to increase the RPM.

What is claimed is:

1. Reaction chamber system for the simultaneous processing of a multitude of liquid, or liquid solutions of, aggressive or hazardous samples, comprising a closed reaction chamber with bottom plate, a platform freely standing on the bottom plate inside the chamber for receiving individual sample containers, with magnetic means fixedly connected to the platform, and a shaking drive, located outside the reaction chamber and being equipped with magnetic driving means providing magnetic coupling to the magnetic means connected to the platform, for driving the platform by the said magnetic coupling.

2. Reaction chamber system according to claim 1, wherein the chamber is provided with means for being emptied.

3. Reaction chamber system according to claim 1, wherein a radiant heater is mounted on the outside the chamber.

4. Reaction chamber system according to claim 1, comprising line connections for filling and emptying the sample containers during processing.

5. Reaction chamber system according to claim 1, comprising electrically non-conducting inserts which prevent the eddy current braking effect in the magnetic coupling area.

6. Reaction chamber system according to claim 1, wherein the reaction chamber has a bottom plate with bearing shells mounted therein and the platform is equipped with bearing journals having a smaller diameter than the bearing shells and standing freely in the bearing shells.

7. Reaction chamber system according to claim 6, wherein the shaking drive is equipped with a multitude of rotating synchronized drivers with driver magnets, and the bearing journals are equipped with integrated shaking magnets.

8. Reaction chamber system according to claim 7, comprising a driver magnet which repels the shaking magnet so that friction decreases as the shaking speed increases.

* * * * *